US010995139B2

(12) United States Patent
Arendt et al.

(10) Patent No.: US 10,995,139 B2
(45) Date of Patent: May 4, 2021

(54) INTERLEUKIN-10 RECEPTOR-2 PEPTIDES, ANTIBODIES, COMPOSITIONS, AND METHODS OF USE THEREOF

(71) Applicant: Wisconsin Alumni Research Foundation, Madison, WI (US)

(72) Inventors: Maria K. Arendt, Madison, WI (US); Mark E. Cook, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/121,770

(22) Filed: Sep. 5, 2018

(65) Prior Publication Data

US 2019/0077859 A1 Mar. 14, 2019

Related U.S. Application Data

(60) Provisional application No. 62/557,443, filed on Sep. 12, 2017.

(51) Int. Cl.
*A61K 39/00* (2006.01)
*A61K 39/385* (2006.01)
*A61K 45/00* (2006.01)
*C07K 16/24* (2006.01)
*C07K 16/10* (2006.01)
*A23L 29/00* (2016.01)
*A61P 33/02* (2006.01)
*A61P 31/04* (2006.01)
*C07K 16/28* (2006.01)
*A61K 38/00* (2006.01)
*A61K 38/20* (2006.01)

(52) U.S. Cl.
CPC ............ *C07K 16/244* (2013.01); *A23L 29/03* (2016.08); *A61K 38/00* (2013.01); *A61K 39/00* (2013.01); *A61P 31/04* (2018.01); *A61P 33/02* (2018.01); *C07K 16/1036* (2013.01); *C07K 16/28* (2013.01); *A23V 2002/00* (2013.01); *A23V 2200/32* (2013.01); *A23V 2250/2044* (2013.01); *A23V 2250/542* (2013.01); *A61K 38/2066* (2013.01)

(58) Field of Classification Search
CPC . A61K 39/001102; A61K 39/00; A61K 47/00
USPC ...................... 424/184.1, 185.1, 194.1, 278.1
See application file for complete search history.

(56) References Cited

U.S. PATENT DOCUMENTS

| 5,102,872 | A | 4/1992 | Singh et al. |
| 5,741,489 | A | 4/1998 | Pimentel |
| 5,989,867 | A | 11/1999 | Knappe et al. |
| 6,608,172 | B1 | 8/2003 | Chiou |
| 7,867,480 | B1 | 1/2011 | Cevec et al. |
| 8,652,457 | B2 | 2/2014 | Sand et al. |
| 9,505,836 | B2 | 11/2016 | Sand et al. |
| 2006/0228448 | A1 | 10/2006 | Bolleau et al. |
| 2009/0022691 | A1 | 1/2009 | Moore et al. |
| 2009/0186038 | A1 | 7/2009 | Reed |
| 2013/0109619 | A1 | 5/2013 | Tarasova et al. |
| 2014/0017248 | A1 | 1/2014 | Sand et al. |
| 2014/0127220 | A1 | 5/2014 | Sand et al. |
| 2015/0037277 | A1 | 2/2015 | Cook et al. |
| 2015/0313964 | A1 | 11/2015 | Cook et al. |
| 2016/0008436 | A1 | 1/2016 | Cook et al. |
| 2016/0280778 | A1 | 9/2016 | Cook et al. |
| 2017/0044251 | A1 | 2/2017 | Sand et al. |

FOREIGN PATENT DOCUMENTS

| WO | 199404174 A1 | 3/1994 |
| WO | 199506657 A1 | 8/1995 |
| WO | 2008086621 A1 | 7/2008 |
| WO | 2015017132 A1 | 2/2015 |
| WO | 2016172722 A1 | 10/2016 |

OTHER PUBLICATIONS

"Anthelmintic Resistance: An Examination of its Growing Prevalence in the U.S. Cattle Herd", Executive Summary of the 2005 Anthelmintic Resistance Roundtable; http://www.merck-animal-health-usa.com/binaries/Anthel_Resist_Exec_Summary_2_tcm96-86774.pdf; 8 pages, (2005).
Alam et al.; "A2A Adenosine Receptor (AR) Activation Inhibits Pro-inflammatory Cytokine Production by Human CD4+ Helper T Cells and Regulates Helicobacter-induced Gastritis and Bacterial Persistence"; Mucosal Immunology; 2(3); pp. 232-242; (2009).
Alba-Hurtado et al.; "Immune Responses Associated with Resistance to Haemonchosis in Sheet"; BioMed Research International; 2013, Article ID 162158; 11 pages; (2013).
Aly et al.; "Agreement Between Bovine Respiratory Disease Scoring Systems for Pre-weaned Dairy Calves"; Animal Health Research Reviews; 15(2); pp. 148-150; (2014).
Arai et al.; "Effects of In Vivo Adminsitration of Anti-IL-10 Monoclonal Antibody on the Host Defence Mechanism Against Murine *Salmonella* Infection"; Immunology; pp. 381-388; (1995).
Arendt et al.; "Interleukin-10 Neutralizing Antibody for Detection of Intestinal Luminal Levels and as a Dietary Additive in Eimeria Challenged Broiler Chicks"; Poultry Science; 95; pp. 430-438; (2016).
Bai et al.; "IL-10 Signaling Blockage Controls Murine West Nile Virus Infection"; PLoS Pathog; 5(10); 13 pages; e1000610.doi:10.1371/journal.ppat.1000610; (2009).
Barnes et al.; "Selection of Different Genotype Larvae and Adult Worms for Anthelmintic Resistance by Persistent and Short-Acting Avermectin/Milbemycins"; International Journal for Parasitology; 31; pp. 720-727; (2001).

(Continued)

*Primary Examiner* — Rodney P Swartz
(74) *Attorney, Agent, or Firm* — Cantor Colburn LLP

(57) ABSTRACT

Described herein are interleukin-10 receptor-2 peptides, antibodies that bind the peptides, compositions including the peptides and antibodies and methods of use of the peptides and antibodies. The interleukin-10 receptor-2 peptide consists of an 8-15 amino acid sequence that includes SEQ ID NO: 1 ((I/V)P(P/K/V/E)P(E/K/R/Q)N(A/V)R), SEQ ID NO: 2 ((S/L/V)PAF(A/P)(K/Q)(G/T/E)(N/T/D)), or SEQ ID NO: 3 (PP(G/T/Q/V)(V/T/A)(R/H/T/S)(GN/NHP/SAA)).

2 Claims, 1 Drawing Sheet

Specification includes a Sequence Listing.

(56) References Cited

OTHER PUBLICATIONS

Bobeck et al.; "Oral Antibodies to Human Intestinal Alkaline Phosphatase Reduce Dietary Phytate Phosphate Bioavailability in the Presence of Dietary 1Alpha-hydroxycholecalciferol"; Poultry Science; 95; pp. 570-580; (2016).
Bobeck et al.; "Oral Peptide Specific Egg Antibody to Intestinal Sodium-dependent Phosphate Co-transporter-2b is Effective at Altering Phosphate Transport in Vitro and in Vivo"; Poultry Science; 94; pp. 1128-1137; (2015).
Bork, Peer; "Powers and Pitfalls in Sequence Analysis: The 70% Hurdle"; Genome Research; 10; pp. 398-400; (2000).
Bowie et al.; "Deciphering the Message in Protein Sequences: Tolerance to Amino Acid Substitutions"; Science; 247(4948); pp. 1306-1310; (1990).
Brown et al.; "Tolerance to Single, But Not Multiple, Amino Acid Replacements in Antibody Vh CDR2"; J. Immunol; 156; pp. 3285-3291; (1996).
Burgess, et al.; "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue"; J.Cell. Biol. 111; pp. 2129-2138; (1990).
Campbell et al.; "Susceptability to Cryptosporidium Parvum Infections in Cytokine- and Chemokine-Receptor Knockout Mice"; Journal of Parasitology; 88(5); pp. 1014-1016; (2002).
Canals, et al.; "Cytokine Profile Induced by a Primary Infection with Ostertagia Ostertagi in Cattle"; Veterinary Immunology and Immunopathology; 58; pp. 63-75; (1997).
Cedillo-Rivera et a; "In Vitro Effect of Nitazoxanide Against Entamoeba Histolytica, Giardia Intestinalis and Trichomonas Vaginalis Trophozoites"; J. Eukaryotic Microbiology; 49(3); pp. 201-208; (2002).
Chen et al; "Oral Administration of a Combination of Select Lactic Acid Bacteria Strains to Reduce the *Salmonella* Invasion and Inflammation of Broiler Chicks"; Poultry Science; 91(9); pp. 2139-2147; (2012).
Coles et al.; "The Detection of Anthelmintic Resistance in Nematodes of Veterinary Importance"; Veterinary Parasitology; 136; pp. 167-185; (2006).
Collier et al.; "Coccidia-induced Mucogenesis Promotes the Onset of Necrotic Enteritis by Supporting Clostridium Perfringens Growth"; Veterinary Immunology and Immunopathology; 112; pp. 104-115; (2008).
Cook, M. E.; "Triennial Growth Symposium: A Review of Science Leading to Host-Targeted Antibody Strategies for Preventing Growth Depression Due to Microbial Colonization"; J. Animal Sci; 89; pp. 1981-1990; (2011).
Cruse et al., Illustrated Dict. of Immunology, 2nd ed., CRC Press, p. 46; (2003).
De Meulenaer et al.; "Isolation and Purification of Chicken Egg Yolk Immunoglobulins: A Review"; Food and Agricultural Immunology; 13(4); pp. 275-288; (2001).
Erova et al.; "Protective Immunity Elicited by Oral Immunization of Mice with *Salmonella enterica* Serovar Typhimurium Braun Lipoprotein (Lpp) and Acetyltransferase (MsbB); Frontiers Cell Infect and Microbiol; vol. 6; Article 148; 14 pages; (2016).
Fawzi et al.; "Intranasal Immunization of Lambs with Serine/Threonine Phosphatase 2A Against Gastrointestinal Nematodes"; Clinical and Vaccine Immunology; 20:9; pp. 1352-1359; (2013).
Feed Terms and Ingredient Definitions from Association of American Feed Control Officials Inc. 2015 Official Publication, Ali Kashani Section Editor; p. 340; (2015); http://aafco.org/publications/PublicationListing.aspx.
Filho et al.; "Humoral and Cellular Immune Response Generated by Different Vaccine Programs Before and After *Salmonella enteritidis* Challenge in Chickens"; Vaccine; 30; pp. 7637-7643; (2012).
Fox et al.; "Nitazoxanide: A New Thiazolide Antiparasitic Agent"; Reviews of Anti-Infective Agents, CID, 40, pp. 1173-1180, (2005).
Ghebremicael et al.; "Association of Interleukin-10 Cluster Genes and *Salmonella* Response in the Chicken"; Poultry Science; 87(1); pp. 22-26; (2008).
Greenspan et al.; "Defining Epitopes: It's Not as Easy as It Seems"; Nature Biotechnology; 7; pp. 936-937; (1999).
Hartog et al.; "Modulation of Human Immune Responses by Bovine Interleukin-10"; PLoS One; 6(3); pp. 1-10; (2011).
Hodek et al.; "Chicken Antibodies—Superior Alternative for Conventional Immunoglobulins"; Proc. Indian Sci Acad; B69(4); pp. 461-468; (2003).
Jones & Martino et al.; "Targeted Localized Use of Therapeutic Antibodies: A Review of Non-systemic, Topical and Oral Applications"; Biotechnology; 36(3); pp. 506-520; (2016).
Josephson et al . . . ; "Noncompetitive Antibody Neutralization of IL-10 Revealed by Protein Engineering and X-Ray Crystallography"; Structure; 10; pp. 981-987; (2002).
Lazar et al.; "Transforming Growth Factor α: Mutation of Aspartic Acid 47 and Leucine 48 Results in Different Biological Activities"; Molecular and Cellular Biology; pp. 1247-1252; (1988).
Lee et al.; "IL-10 Suppresses Bactericidal Response of Macrophages Against *Salmonella typhimurium*"; Journal of Microbiology; 49(6); pp. 1050-1053; (2011).
Li, Robert W. et al.; "Localized Complement Activation in the Development of Protective Immunity Against Ostertagia Ostertagi Infections in Cattle"; Veterinary Parasitology; 174; pp. 247-256; (2010).
Li, Robert W., et al.; "Local Inflammation as a Possible Mechanism of Resistance to Gastrointestinal Nematodes in Angus Heifers"; Veterinary Parasitology; 145; pp. 100-107p (2007).
MacCallum et al.; "Antibody-antigen Interactions: Contact Analysis and Binding Site Topography"; J. Mol. Biol. 262; pp. 732-745; (1996).
Nuflor; "Bovine Respiratory Diseases: A New Look at Causes and Signs of Disease"; found in MERCK Animal Health ; http://www.nuflor.com/diseases/brd-nlac.asp; 4 pages; printed Mar. 3, 2017.
Paul, Fundamental Immunology, Third Edition (textbook), "Fv Structure and Diversity in Three Dimensions" pp. 292-295; Raven Press, New York (1993).
Rothwell et al.; "Cloning and Characterization of Chicken IL-10 and Its Role in the Immune Response to Eimeria Maxima"; Journal of Immunology; 173; pp. 2675-2682; (2004).
Salazar et al.; "Systemic *Salmonella* Infection Requires Interleukin 10 Production in Mice"; Front. Immunol. Conference Abstract:IMMUNOCOLOMBIA2015 at the 11th Congress of the Latin American Association of Immunology, 2015; doi: 10.3389/conf.fimmu.2015.05.00144.
Sand et al.; "Oral Antibody to Interleukin-10 Reduces Growth Rate Depression Due to Eimeria Supp. Infection in Broiler Chickens"; 95(2); pp. 439-446; (2016).
Sand et al._"Oral Antibody to Interleukin-10 Prevents Growth Suppression by Coccidia Infection"; from Poultry Science Association 101st Annual Meeting Abstracts; Abstract P310; Jul. 9-12, 2012; Poult.Sci. 91(suppl.1) p. 107.
Setta et al.; "Early Immune Dynamics Following Infection With *Salmonella enterica* Serovars Enteridis, Infantis, Pullorum and Gallinarum: Cytokine and Chemokine Gene Expression Profile and Cellular Changes of Chicken Cecal Tonsils"; Comparative Immunology pp. 397-410; (2012).
Silva et al.; Blocking the Receptor for Interleukin 10 Protects Mice from Lethal Listeriosis; Antimicrobial Agents and Chemotherapy; pp. 1312-1314; (2001).
Symonds et al.; "Bifidobacterium Infantis 35624 Protects Against *Salmonella*-Induced Reductions in Digestive Enzyme Activity in Mice by Attenuation of the Host Inflammatory Response"; Clinical and Translational Gastroenterology; 3, e15; 10 pages; (2012) doi:10.1038/ctg.2.
Vajdos et al.; "Comprehensive Functional Maps of the Antigen-binding Site of an Anti-ErbB2 Antibody Obtained with Shotgun Scanning Mutagenesis"; J. Mol. Biol. 320, pp. 415-428; (2002).
Wei et al.; "*Salmonella enterica* Serovar Typhi Plasmid Impairs Dendritic Cell Responses to Infection"; Curr Microbiol; 65; pp. 133-140; (2012).

(56) References Cited

OTHER PUBLICATIONS

International Search Report dated Dec. 6, 2018; International Application No. PCT/US2018/049451; International Filing Date: Sep. 5, 2018 (7 pages).
Pereira, et al.; "Requirement of Dual Stimulation by Homologous Recombinant IL-2 and Recombinant IL-12 for the invitro Production of Interferon Gamma by Canine Peripheral Blood Mononuclear Cells"; BMC Research Notes; pp. 460-469; (2014).
Reineke, et al.; "Mapping of the Interleukin-10/Interleukin-10 Receptor Combining Site"; Protein Science; vol. 7, pp. 951-960; Cambridge University Press; (1998).
Written Opinion dated Dec. 6, 2018; International Application No. PCT/US2018/049451; International Filing Date: Sep. 5, 2018 (10 pages).
Yoon et al; "Conformational Changes Mediated Interleukin-10 Receptor 2 (IL-10R2) Binding to IL-10 and Assembly of the Signaling Complex"; The Journal of Biological Chemistry; 281(46); pp. 35088-35096; (2006).
Williams, R.B.; "Anticcoccidial Vaccines for Broiler Chickens: Pathways to Success"; Avian Pathology; 31(4); pp. 317-353; (2002).
Xystrakis et al.; "Reversing the Defective Induction of IL-10-secreting Regulatory T Cells in Glucocorticoid-resistant Asthma Patients"; J. Clin. Invest.; 116; pp. 146-155; (2006).
Yadav et al.; "Gastrointestinal Stability of Therapeutic Anti-TNF Alpha IgG1 Monoclonal Antibodies"; International Journal of Pharmaceutics; 502; pp. 181-187; (2016).
Yazwinski et al.; "Fecal Egg Count Reduction and Control Trial Determinations of Anthelmintic Efficacies for Several Parasiticides Utilizing a Single Set of Naturally Infected Calves"; Veterinary Parasitology; 164; pp. 232-241; (2009).

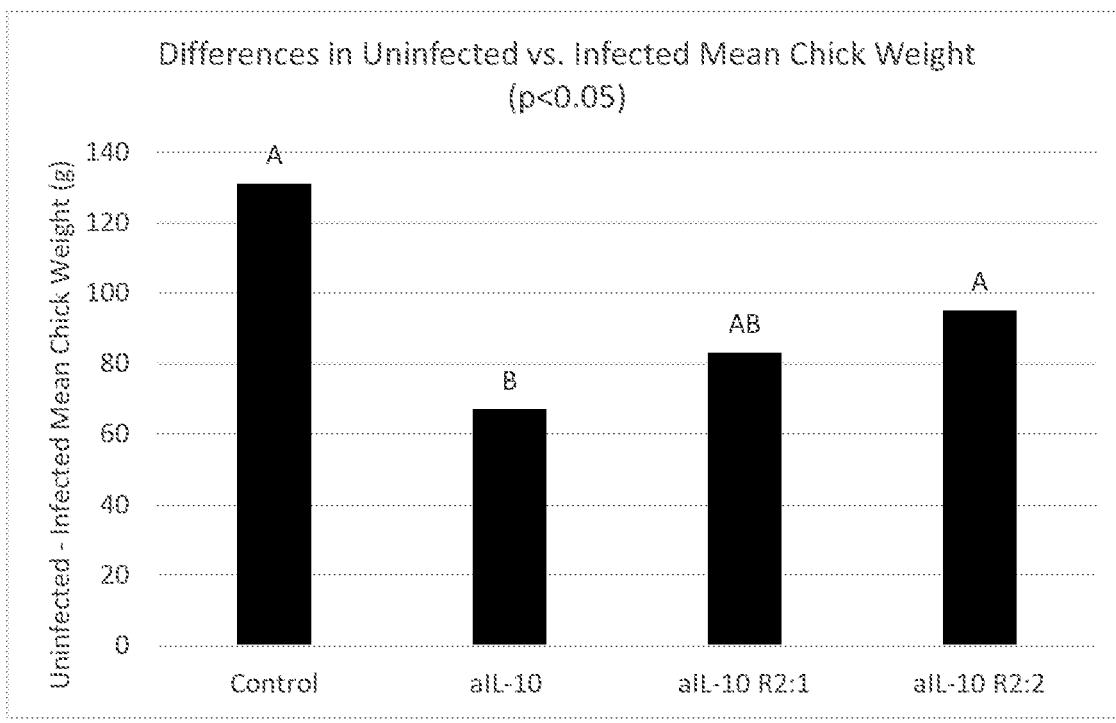

INTERLEUKIN-10 RECEPTOR-2 PEPTIDES, ANTIBODIES, COMPOSITIONS, AND METHODS OF USE THEREOF

CROSS-REFERENCE TO RELATED APPLICATIONS

This application claims priority to U.S. Provisional Application 62/557,443 filed on Sep. 12, 2017, which is incorporated herein by reference in its entirety.

FIELD OF THE DISCLOSURE

The present disclosure is related to interleukin-10 receptor-2 peptides, antibodies that bind the peptides, and their use to reduce foodborne or environmental pathogens in the intestines of a subject in need thereof.

BACKGROUND

Foodborne and environmental pathogens can be consumed by humans and animals, resulting in symptoms such as diarrhea and intestinal infection. Zoonotic diseases associated with *Salmonella* species, for example, are transmitted to humans ingesting infected animals such as poultry or animal products such as milk. In addition, foodborne and environmental pathogens result in growth suppression and disease in animals raised for food production as well as domesticated animals.

Coccidiosis, for example, is a common protozoan infection in livestock species (e.g., poultry, swine and calves). Coccidiosis in poultry alone is estimated to cost the poultry industry $1 billion a year in reduced animal performance. The two approaches for controlling coccidiosis are the use of drugs to prevent and treat coccidiosis or to vaccinate the birds using an attenuated coccidiosis vaccine. However, the vaccine also suppresses animal performance. Hence, an additive that reduces Coccidiosis while minimizing growth depression either during Coccidiosis infection or vaccination is desired.

Previously, peptides corresponding to the antigenic solvent-exposed regions of IL-10 were identified. It was shown that anti-interleukin-10-specific antibodies that bind the peptides reduce gastrointestinal protozoa such as Coccidia in animals such as poultry (U.S. Pat. No. 9,505,836); reduce *Salmonella* in the intestines of animals such as poultry (U.S. Publication No. 2015/0313964); control parasitic worms in the intestine of herbivorous mammals such as bovines (U.S. Publication No. 2016/0008436); and reduce symptoms of respiratory disease in pre-weaned milk-fed mammals (U.S. Publication No. 2016/0280778).

What is needed are alternative compositions and methods to reduce foodborne or environmental pathogens in the intestines of a subject in need thereof.

BRIEF SUMMARY

In one aspect, an interleukin-10 receptor-2 peptide is covalently linked to a carrier peptide, wherein the interleukin-10 receptor-2 peptide consists of an 8-15 amino acid sequence that includes SEQ ID NO: 1 ((I/V)P(P/K/V/E)P(E/K/R/Q)N(A/V)R), SEQ ID NO: 2 ((S/L/V)PAF(A/P)(K/Q)(G/T/E)(N/T/D)), or SEQ ID NO: 3 (PP(G/T/Q/V)(V/T/A)(R/H/T/S)(GN/NHP/SAA)).

In another aspect, an isolated antibody specifically binds an interleukin-10 receptor-2 peptide, wherein the interleukin-10 receptor-2 peptide consists of an 8-15 amino acid sequence that includes SEQ ID NO: 1 ((I/V)P(P/K/V/E)P(E/K/R/Q)N(A/V)R), SEQ ID NO: 2 ((S/L/V)PAF(A/P)(K/Q)(G/T/E)(N/T/D)), or SEQ ID NO: 3 (PP(G/T/Q/V)(V/T/A)(R/H/T/S)(GN/NHP/SAA)).

In yet another aspect, a dried egg yolk comprises an antibody that specifically binds an interleukin-10 receptor-2 peptide, wherein the interleukin-10 receptor-2 peptide consists of an 8-15 amino acid sequence that includes SEQ ID NO: 1 ((I/V)P(P/K/V/E)P(E/K/R/Q)N(A/V)R), SEQ ID NO: 2 ((S/L/V)PAF(A/P)(K/Q)(G/T/E)(N/T/D)), or SEQ ID NO: 3 (PP(G/T/Q/V)(V/T/A)(R/H/T/S)(GN/NHP/SAA)), wherein the antibody that specifically binds the interleukin-10 receptor-2 peptide in the egg yolk comprises a total 1 to 10% by weight of the total IgY in the egg yolk.

In a further aspect, included are compositions comprising the isolated antibodies and dried egg yolk, such as food and feed additives and food and feed compositions.

In another aspect, a method of reducing a foodborne or environmental pathogen in the intestines of a subject in need thereof comprises administering to the subject a composition comprising the isolated antibody or dried egg yolk described above, wherein the isolated antibody is administered in an amount effective to reduce the foodborne or environmental pathogen in the intestines of the subject.

BRIEF DESCRIPTION OF THE DRAWINGS

FIG. 1 shows differences in uninfected versus infected mean chick weight at day 21 of age. A-B means with different labels within a column were significantly different (P<0.05). Difference in mean chick weight was calculated by subtracting uninfected–coccidia infected mean chick weights and were measured in grams.

The above-described and other features will be appreciated and understood by those skilled in the art from the following detailed description, drawing, and appended claims.

DETAILED DESCRIPTION

Antibodies that specifically bind interleukin-10 (IL-10) and reduce foodborne or environmental pathogens in the intestines of subjects have been described and are well-suited for their intended purpose. However, it is possible that anti-IL-10 antibodies can interfere with functions other than IL-10 receptor binding. Advantageously, targeting the IL-10 receptor could interfere not only with IL-10 binding, but also the binding of IL-10 mimics such as IL-10 expressing viruses. Thus, antibodies that bind IL-10 receptors may have advantages over the antibodies that bind IL-10 peptides.

Unexpectedly, it was found that anti-IL-10-receptor-2 (IL-10 R2; also known as IL-10 R beta (β) antibodies, but not anti-IL-10 receptor-1 antibodies (IL-10 R1; also known as IL-10 R alpha (α)) improved weight gain in the face of a Coccidia infection in chickens. IL-10 R1 has been shown to reside on the apical surface of enterocytes, thus it was expected that blocking this receptor would provide similar effects to anti-IL-10 antibodies. The location of IL-10 R2 in the intestines has not been described. In addition, IL-10 R1 has a higher affinity for IL-10 than IL-10 R2. It was thus completely unexpected that anti-IL10 R2 and not anti-IL-10 R1 antibodies reduce foodborne or environmental pathogens in the intestines of subjects.

IL-10 R2 peptides were identified by examining the crystal structure of IL-10 bound to IL-10 R2 and selecting IL-10 R2 peptides in the binding interface. In an aspect, a IL-10 R2 peptide comprises an 8-15 amino acid sequence that includes SEQ ID NO: 1 ((I/V)P(P/K/V/E)P(E/K/R/Q)N(A/V)R), SEQ ID NO: 2 ((S/L/V)PAF(A/P)(K/Q)(G/T/E)(N/T/D)), or SEQ ID NO: 3 (PP(G/T/Q/V)(V/T/A)(R/H/T/S)(GN/NHP/SAA)). Exemplary peptides of SEQ ID NOs. 1-3 are provided in Table 1:

TABLE 1

IL-10-R2 peptide sequences

| Species | IL-10 R2: 1 Homologous Peptide | SEQ ID NO: | IL-10 R2: 2 Homologous Peptide | SEQ ID NO: |
|---|---|---|---|---|
| *Homo sapiens, P. troglodytes, M. mulatta* | VPPPENVR | 4 | SPAFAKGN | 18 |
| *Canis lupus* | VPPPKNVR | 5 | LPAFPKGT | 19 |
| *Felis catus* | VPPPENVR | 6 | VPAFPKGN | 20 |
| *Bos taurus* | VPPPENVR | 7 | SPAFPKGN | 21 |
| *Ovis aries* | IPPPENVR | 8 | SPAFPKGN | 22 |
| *Capra hircus* | IPPPENVR | 9 | SPAFPKGN | 23 |
| *Equus caballus* | VPPPENVR | 10 | SPAFPKGD | 24 |
| *Sus scrofa* | VPPPENVR | 11 | SPAFPQGD | 25 |
| *Mus musculus* | IPPPEKVR | 12 | VPAFPKTN | 26 |
| *Rattus norvegicus* | IPPPENVR | 13 | VPAFPKEN | 27 |
| *Gallus Gallus* | VPKPRNAR | 14 | PPGVRKGN | 28 |
| *Meleagris gallopavo* | VPKPRNAR | 15 | PPTVHKGN | 29 |
| *Danio rerio* | VPVPENVR | 16 | PPQTTNNHP | 30 |
| *Xenopus tropicalis* | VPEPQNVR | 17 | PPVASGSAA | 31 |

The IL-10 R2 peptide may be conjugated to a carrier such as a carrier protein, for example, bovine gamma globulin or keyhole limpet hemocyanin.

As used herein, the term "peptide" includes the peptide as well as pharmaceutically acceptable salts of the peptide. "Amino acid residue" means the individual amino acid units incorporated into the peptides of the disclosure. As used herein, the term "amino acid" means a naturally occurring or synthetic amino acid, as well as amino acid analogs, stereoisomers, and amino acid mimetics that function similarly to the naturally occurring amino acids.

As used herein, the term "antibody", or "immunoglobulin", encompasses naturally occurring antibodies, such as polyclonal and monoclonal antibodies, as well as artificial or synthetic antibodies or genetically engineered forms of antibodies, including single chain antibodies, chimeric, and bifunctional antibodies, as well as fragments thereof.

The term "isolated antibody" as used herein, refers to an antibody that is substantially free of other naturally associated molecules, or substantially free of antibodies having different antigenic specificities.

Also included are isolated antibodies that specifically bind the IL-10 R2 peptides disclosed herein. In an aspect, an isolated antibody specifically binds an IL-10 R2 peptide, wherein the IL-10 R2 peptide consists of an 8-15 amino acid sequence that includes SEQ ID NO: 1 ((I/V)P(P/K/V/E)P(E/K/R/Q)N(A/V)R), SEQ ID NO: 2 ((S/L/V)PAF(A/P)(K/Q)(G/T/E)(N/T/D)), or SEQ ID NO: 3 (PP(G/T/Q/V)(V/T/A)(R/H/T/S)(GN/NHP/SAA)). The peptide of SEQ ID NO. 1 can have any one of SEQ ID NOs. 4-17; the peptide of SEQ ID NO: 2 can have any one or more of SEQ ID NOs: 18-27; and the peptide of SEQ ID NO: 3 can have any one or more of SEQ ID NOs: 28-31.

In an aspect, the isolated antibody is an IgY antibody.

In an aspect, a dried egg yolk comprises an antibody that specifically binds an IL-10 R2 peptide, wherein the IL-10 R2 peptide consists of an 8-15 amino acid sequence that includes SEQ ID NO: 1 ((I/V)P(P/K/V/E)P(E/K/R/Q)N(A/V)R), SEQ ID NO: 2 ((S/L/V)PAF(A/P)(K/Q)(G/T/E)(N/T/D)), or SEQ ID NO: 3 (PP(G/T/Q/V)(V/T/A)(R/H/T/S)(GN/NHP/SAA)). In an aspect, the antibody that specifically binds an IL-10 R2 peptide in the egg yolk comprises a total of 1 to 10% by weight of the total IgY in the egg yolk The peptide of SEQ ID NO. 1 can have any one of SEQ ID NOs. 4-17; the peptide of SEQ ID NO: 2 can have any one or more of SEQ ID NOs: 18-27; and the peptide of SEQ ID NO: 3 can have any one or more of SEQ ID NOs: 28-31. In an aspect, the water content of the dried avian egg yolk is less than 5 wt % of the total weight of the dried avian egg yolk.

The present disclosure is further directed to generating antibodies that specifically bind to the IL-10 R2 peptides. In an embodiment, an antibody is generated by administering the IL-10 R2 peptides described above to an animal. Suitable animals to administer the IL-10 R2 peptides for generating the antibodies include, for example, poultry. Exemplary poultry include chickens, turkeys, ducks, quail, and pheasant. Specific poultry include turkeys and chickens. Additional animals include livestock animals such as cows, pigs, sheep, and fish.

Exemplary methods for administering the IL-10 R2 peptides to the animal include injection and oral administration. Injection and oral administration optionally include use of an adjuvant such as, for example, Freund's Complete adjuvant and Cholera toxin. Administration optionally further includes conjugation of the IL-10 R2 peptide to a carrier protein such as, for example, bovine gamma globulin or keyhole limpet hemocyanin.

In one embodiment, antibodies to the IL-10 R2 peptides are generated by an animal (referred to herein as the "producer animal"). When the animal is an avian animal, as known by those skilled in the art, the antibodies generated are passed to the egg, and may specifically be concentrated in the egg yolk of the avian producer animal. Alternatively, antibodies of the present disclosure may be isolated from the animal itself such as from serum.

In one embodiment, the antibody is an avian egg yolk antibody. Egg yolks derived from a laying hen are inexpensive, convenient and can be safer to handle as compared to the hyperimmunized mammalian sera. Also, egg yolk antibodies are able to stand up to the scrutiny under modern animal protection regulations. Immunoglobulin Y (IgY) is an avian immunoglobulin.

To produce avian egg yolk antibodies, the IL-10 R2 peptides are injected into laying fowl, such as hens, preferably at various intervals, to induce an immune response. The hens may be injected intramuscularly or subcutaneously. The specific mode of injection is not essential. It is well known that the IgY antibodies produced by the hens in response to such an immune challenge are transferred and concentrated in the egg yolk.

Once the eggs are harvested, the eggs may be further processed to isolate the egg yolk, which itself may be further processed. The liquid egg yolk may be encapsulated or otherwise used in oral dosage forms. The egg yolk may be dried by spray or refractant drying methods, and the resulting dried powder may be encapsulated or otherwise used in oral dosage forms.

Alternatively, a procedure of partial purification or fractionation may be carried out to remove the majority of the non-aqueous bio-molecules and granules and optionally the majority of other proteins in the egg yolk. Exemplary purification techniques include the use of PEG, dextran sulfate or a natural gum, such as sodium alginate, carrageenan and xanthan gum, to coprecipitate the undesired substances, and the use of an aqueous buffer or water to obtain an aqueous phase rich with antibodies.

In a specific embodiment, the yolk is separated from the egg white, and then washed with distilled water to remove as much albumen as possible. The vitelline membrane encasing the yolk is punctured, and the separated yolk fraction is then diluted with an effective amount of an aqueous buffer or water to form a suspension of the egg yolk. The collected egg yolk may be diluted with an aqueous buffer solution or distilled water in a ratio of about 1:2 to about 1:40 v/v, and more specifically, in a ratio of about 1:5 to about 1:30 v/v. For efficient recovery of yolk antibodies, the pH is about 5-7. Desirably, the temperature in this step is within about 0° C. to about 60° C. The suspension of the egg yolk is gently agitated to form a homogenous mixture, and then allowed to stand for a period of time sufficient to form the aqueous and non-aqueous phases. The water insoluble materials, including non-aqueous bio-molecules such as lipoproteins, phospholipids, sterols and the like, are then removed from the aqueous yolk suspension by centrifugation. The resulting antibody-containing supernatant may then be separated from the viscous precipitate by decanting, suctioning, or other like methods known in the art.

Optionally, the yolk supernatant is further treated with a high concentration of a non-denaturing salt to induce precipitation of the antibodies. Examples of the salts useful for precipitation of the yolk antibodies include, but are not limited to, NaCl, $Na_2SO_4$, $(NH_4)_2SO_4$, KCl, $CaCl_2$), and $MgSO_4$. Specific salts include $Na_2SO_4$ and $(NH_4)_2SO_4$. The salt concentration for precipitating antibodies depends on the type of the salt. In one embodiment, the salt is present in an amount of higher than 15% and lower than 35% by weight, specifically between 20% and 30% by weight of the salt, on the basis of the final volume of the yolk supernatant.

Alternatively, the antibodies may be purified or isolated using any conventional technique such as by immunoaffinity purification.

In one embodiment, egg yolk antibodies are prepared by the following method. Laying hens are inoculated with IL-10 R2 peptide. Optionally, an adjuvant is administered in conjunction with the IL-10 R2 peptide to enhance the immunization. An adjuvant useful for this purpose is a water-in-oil emulsion adjuvant such as complete Freund's adjuvant. The IL-10 R2 peptide causes the hens to produce anti-IL-10 R2 antibodies which are passively transferred into the egg yolk of eggs laid by the hens.

Egg yolks or whole eggs containing the anti-IL-10 antibody can be collected and homogenized to form an emulsion. The resulting emulsion can be dried to form a powder containing the anti-IL-10 R2 antibody. This powder can then be formulated in a manner appropriate to the administration route and then administered to the desired animals using methods known in the art. The preparation is preferably administered orally, such as in an oral dosage form or in a supplement to the animal's diet.

The antibodies that specifically bind to IL-10 R2 peptides may be isolated and purified from animal serum or egg using a suitable method known in the art. Such methods include affinity chromatography, as well as other suitable methods for antibody isolation and purification known in the art and described in U.S. Pat. No. 6,608,172 and De Meulenaer et al., "Isolation and Purification of Chicken Egg Yolk Immunoglobulins: A Review," Food and Agricultural Immunology, Vol. 13(4), 2001, hereby incorporated by reference to the extent that they are consistent herewith. In one particularly suitable embodiment, the production animal is an avian animal such as a chicken, turkey, duck, or quail, and the antibody is isolated from the egg yolk of the egg of the avian animal.

In one embodiment, the egg yolk or serum including the antibodies are further dried to form a powder including the antibodies. The whole egg, egg yolk or parts of the egg may be spray dried. Serum may be separated from whole blood according to methods known by those skilled in the art. Spray drying of egg and serum may be performed using known spray drying methods and commercially available spray drying equipment. Dry egg and serum powders may also be prepared by lyophilization. The dried egg, egg yolk or serum powder may then be introduced into animal feeds as a feed additive to transfer antibodies to an animal.

The present disclosure is further generally directed to animal feed additives and food additives including the IL-10 R2 peptides, or isolated antibodies which specifically bind to IL-10 R2 peptides. The food or feed additives optionally include a carrier.

As used herein, a food or feed additive is a substance that is added to food or feed to enhance the properties of the food or feed.

The present disclosure also contains foods and feeds containing the IL-10 R2 peptides, or isolated antibodies which specifically bind to IL-10 R2 peptides.

As used herein, the term "feed" broadly refers to a material, liquid or solid, that is used for nourishing an animal, and for sustaining normal or accelerated growth of an animal including newborns or young and developing animals. The term includes a compound, preparation, mixture, or composition suitable for intake by an animal. Specifically, the feed is suitable for poultry such as quail, ducks, turkeys, and chickens and animals such as cattle, horses, sheep and goats; for fish; or for companion animals.

A feed composition comprises a basal feed composition and one or more feed additives. The term "basal feed composition" refers to a food composition combinable with additives such as the peptides and antibodies described herein. Basal animal feed compositions may include components such as proteins, grains, flavor compositions, vitamins, minerals, preservatives, and the like. Basal feed compositions can be suitable for ingestion by a target animal. The term "feed additive" as used herein refers to components included in small quantities for the purpose of fortifying basic feed with nutrients, stimulants, medicine, or to promote feed intake or alter metabolism. Feed additives include pre-mixes of biological compositions, or in the present disclosure, pre-mixes of IL-10 peptide or isolated antibody that specifically binds to IL-10 peptide.

In one embodiment, the present disclosure includes an animal feed additive including IL-10 R2peptides including the amino acid sequence of SEQ ID NOs: 1-31.

In another embodiment, the present disclosure includes an animal feed additive including isolated antibodies that specifically bind to the IL-10 R2 peptide including the amino acid sequence of SEQ ID NOs: 1-31.

The IL-10 R2 peptides or isolated antibodies which specifically bind to IL-10 R2 peptides may be added to an animal feed as a feed additive or mixed into an animal feed by a method known in the art for mixing feed additives and animal feed. In one embodiment, the IL-10 R2 peptide or isolated antibody which specifically binds to the IL-10 R2 peptide is directly added to the animal feed or mixed with the animal feed just prior to feeding the animal. In another embodiment, since feeds may be pelleted or extruded, the IL-10 R2 peptide or isolated antibody which specifically binds to the IL-10 R2 peptide may be coated on the surface of feed (pellet) after the feed has been pelleted or extruded (post pelleted application) in order to maintain functional properties of the IL-10 R2 peptide or isolated antibody which specifically binds to the IL-10 R2 peptide. The addition of the IL-10 R2 peptide or isolated antibody which specifically binds to the IL-10 R2 peptide post pelleting can be aided by mixing the IL-10 R2 peptide or isolated antibody which specifically binds to the IL-10 R2 peptide in water, oil, or another suitable carrier and spraying it on the pellets as they exit the pellet die.

The amount of the IL-10 R2 peptide or isolated antibody that specifically binds to IL-10 R2 peptide added and/or mixed with the animal feed depends on the feeding regimen and the type of feed for the animal, and may be determined by those skilled in the art. Typically, the amounts of IL-10R2 peptides and/or isolated antibodies to IL-10 R2 peptide to be used in an animal feed are summarized in Table 2 below. Antibody prepared using other sources may be calculated as equivalents using Table 2.

TABLE 2

Dose of Anti-IL-10 R2 Antibody in Animal Feed (mg/Kg diet) prepared using egg yolk antibody.

| Source | Low Dose | High Dose |
|---|---|---|
| Affinity purified anti-peptide | 0.0015 | 0.5 |
| Anti-peptide IgY | 0.015 | 50 |
| Dry Immune Yolk | 0.8 | 4000 |
| Dried Immune Whole Egg | 1.5 | 7500 |

The doses shown are based on the amount of epitope specific antibody in total IgY (1 to 10%), the amount of IgY in egg (5-10 mg/Kg of feed), antibody losses due to drying storage and gastrointestinal degradation.

An animal feed may further include optional ingredients including vitamins, minerals, antibiotics, lipids, carbohydrates, proteins, antioxidants, and amino acids.

Exemplary vitamins include Vitamin A, Vitamin B, Vitamin D, Vitamin E, and Vitamin K. Exemplary minerals include calcium, phosphorus, sodium, potassium, magnesium, chlorine, cobalt, iodine, iron, manganese, copper, molybdenum, zinc and selenium. Common mineral supplements used in poultry feed, for example, include limestone, bone meal, oyster shell, sodium chloride, dicalcium phosphate, manganese sulphate, potassium iodide, and superphosphate.

In some embodiments, one or more antibiotics may be included in the animal feed along with the feed additive. Exemplary antibiotics include penicillin, streptomycin, tetracyclines, zinc bacitracin and aureomycin.

Exemplary lipids include oil seeds, oils and lipids derived from plants or animals. Sources of oilseeds, oils and lipids include corn, soybean, cotton, lupin, peanut, sunflower, canola, sesame seed oil, olive oil, copra and coconut oil, palm kernels and palm oil, casein, butterfat, lard, fish oils, linseed and oil, tuna oil, tallow and yellow grease, and mixtures thereof.

Exemplary carbohydrates include starch, cellulose, pentosans, other complex carbohydrates, corn, milo, barley, rye, oats, wheat, wheat middlings, and various grain-by-products.

Exemplary sources of protein include protein obtained from meat meal or fish meal, liquid or powdered egg, fish solubles, whey, milk protein, rice, milo, millet, corn, oats, barley, wheat, rye, wheat bran and/or middlings, soybeans, sesame seeds, peas and beans, sunflower seeds, wheat germ, alfalfa seed, flaxseed, yeast, earthworms, and fish.

Exemplary amino acids include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cystein ethyl HCl, and analogs, and salts thereof.

Exemplary antioxidants include beta-carotene, Vitamin E, Vitamin C, and tocopherol, or synthetic antioxidants.

Specifically, the animal feed including the feed additive of either IL-10 R2 peptide or isolated antibody is a feed for avian species such as quail, ducks, turkeys, and chickens, as well as feeds for mammals including swine, cows, dogs, cats, rabbits and the like. As used herein, the term "food" broadly refers to a material, liquid or solid, that is used for nourishing a human. The term includes a compound, preparation, mixture, or composition suitable for intake by humans. A food composition comprises a basal food composition. The term "basal food composition" refers to a food composition combinable with additives such as the peptide and antibodies described herein.

Exemplary basal food compositions include milk, juice, formula, and solid foods such as snack food consumable by humans including human children.

Also included herein are pharmaceutical compositions comprising the IL-10 R2 peptides and/or anti IL-10 R2 antibodies and a pharmaceutically acceptable excipient.

In an aspect, a composition comprises egg yolk, wherein the egg yolk comprises an antibody that specifically binds an IL-10 R2 peptide, wherein the IL-10 R2 peptide consists of an 8-15 amino acid sequence that includes SEQ ID NO: 1 ((I/V)P(P/K/V/E)P(E/K/R/Q)N(A/V)R), SEQ ID NO: 2 ((S/L/V)PAF(A/P)(K/Q)(G/T/E)(N/T/D)), or SEQ ID NO: 3 (PP(G/T/Q/V)(V/T/A)(R/H/T/S)(GN/NHP/SAA). The peptide of SEQ ID NO. 1 can have any one of SEQ ID NOs: 4-17; the peptide of SEQ ID NO: 2 can have any one or more of SEQ ID NOs: 18-27; and the peptide of SEQ ID NO: 3 can have any one or more of SEQ ID NOs: 28-31. In an aspect, the antibody that specifically binds an IL-10 R2 peptide in the egg yolk comprises a total 1 to 10% by weight of the total IgY in the egg yolk.

The composition comprising egg yolk can be in the form of an animal feed or food additive composition, a food or feed composition, or a pharmaceutical composition as described above.

In an aspect, a method of reducing a foodborne or environmental pathogen in the intestines of a subject in need thereof, comprises administering to the subject a composition comprising the Il-10 R2 peptides or anti-Il-10 R2 antibodies as described herein, wherein the peptide or isolated antibody is administered in an amount effective to reduce the foodborne or environmental pathogen in the intestines of the subject.

As used herein, a foodborne pathogen is a pathogen transmitted to a human or animal host via food. For example, most cases of campylobacteriosis, the infection caused by

*Campylobacter* bacteria, are associated with humans eating raw or undercooked poultry and meat or from cross-contamination of other foods by these items. Environmental pathogens include microorganisms that normally spend a substantial part of their lifecycle outside their human or animal hosts, but when introduced to humans or animals cause disease or symptoms such as reduced weight gain with measurable frequency. *Salmonella* is an environmental pathogen of chickens that often does not produce symptoms in the infected poultry, but is a serious problem when passed to humans through consumption of poultry products.

Exemplary foodborne or environmental pathogens include a protozoan, a bacteria, a parasitic worm, a virus, or a combination comprising at least one of the foregoing.

Gastrointestinal protozoa include parasites from the kingdom Protozoa. In a suitable embodiment, the protozoa treated by the presently disclosed methods may be from Apicomplexa. Suitable Apicomplexa may be, for example, Coccidiasina. In a particularly suitable embodiment, the protozoa is Eimeriorina such as, for example, Eimeriidae and Cryptosporidiidae. In a particularly suitable embodiment, the protozoa is selected from the group consisting of *Cryptosporidium, Eimeria acervulina, Eimeria tenella, Eimeria maxima* and *Eimeria brunetti*.

Coccidiosis, for example, causes growth suppression and other disease effects in poultry. Coccidia is generally not transferrable to humans consuming poultry products. Because young birds are more susceptible to Coccidiosis than more mature birds, Coccidiosis is generally treated by providing anti-Coccidial agents in starter feeds. In commercial chicken production, for example, starter feeds are generally used only in the first 3 weeks of a chick's life due to the early susceptibility to Coccidiosis, the expense of feed containing additives, and concerns about carry-over of agents into produced meat. In turkeys, starter feeds may be used for 6-8 weeks after hatch. Anti-IL-10 R2 antibodies reduce growth suppression typical of gastrointestinal protozoan-infected animals.

Infection with *Salmonella* bacteria often does not produce symptoms in the infected poultry, but is a serious problem when passed to humans through consumption of poultry products. An additive that can reduce *Salmonella* in the intestines of poultry particularly when used in the final 1 to 4 weeks prior to harvest would greatly reduce the passage of *Salmonella* from poultry to humans through consumption of poultry meat. The IL-10 R2 peptides and anti-IL-10 R2 peptide antibodies represent a new strategy to prevent transmission of *Salmonella* to humans by reducing *Salmonella* in the intestines of poultry.

In an aspect, wherein subject is a chicken, the peptide comprises SEQ ID NO: 14 or 28, and the foodborne or environmental pathogen is an *Eimeria* species, *Cryptosporidium*, a *Salmonella* species, or a combination thereof.

Young pre-weaned mammals such as dairy calves are susceptible to dairy calf pneumonia, referred to as Bovine Respiratory Disease Complex. Bovine respiratory disease complex (BRD) is a significant cause of morbidity, mortality and animal welfare concern and costs the industry between $800-900 million annually. Antibiotic treatment is costly, recurrence rates are high, the development of refractory sequelae are common, and antibiotic resistance is a concern. Thus, there is a need for improved treatment of pre-weaned mammals that are susceptible to respiratory infections, including mammals of a genus *Bos* (calves/cows), *Ovis* (lambs/sheep), *Capra* (kids/dairy goats), *Sus* (piglets/pigs) and *Bubalus* (calf/water buffalo), particularly milk-fed mammals.

In one embodiment, a method of reducing a symptom of respiratory disease in a pre-weaned milk-fed mammal comprises orally administering to the pre-weaned milk-fed mammal an effective amount of an IL-10 R2 peptide or an isolated antibody that specifically binds an IL-10 R2 peptide. Administration may be initiated between birth and weaning, such as within 1 to 3 days of birth, and wherein administration is performed at least once daily for a period of 7 days to 7 weeks, specifically 7 days to three, four, five or six weeks, more specifically 7 days to 2 weeks. In one embodiment, the treated mammal is a bovine that exhibits reduced evidence of respiratory disease at 56 days of age compared to a control untreated pre-weaned bovine. In certain aspects, administration of the IL-10 R2 peptide or anti-IL-10 R2 antibody is stopped after the treatment period, e.g., a 7 day to 7 week treatment period. In another aspect, administration of the IL-10 R2 peptide or anti IL-10 R2 antibody is not restarted for at least 1 to 14 days, specifically 7 to 14 days. In a specific aspect, the pre-weaned milk-fed mammal is a Bovine (a calf), and the respiratory disease is bovine respiratory disease. In other aspects, the pre-weaned milk-fed mammal is a sheep, a dairy goat, or a water buffalo.

As used herein, the term weaning means the practice of separating a mammal such as a calf from its source of milk. Calves are generally separated from their mothers shortly after birth and are fed whole milk or a milk replacer until weaning from their milk source, generally at 28 to 56 days of age. Calves that are raised apart from their mothers can be referred as housed calves and are generally housed in individual pens or in small groups. Nursing calves, however, can also be supplemented with milk or milk replacer. Thus, a pre-weaned mammal is a baby mammal that receives the majority of its nutrition from milk. As used herein, milk-fed means that a mammal is fed either whole milk, waste milk or milk replacer as their primary source of nutrition. Milk replacer, in the case of calves, generally includes protein such as whey protein or casein, but can also contain soy protein for example. In addition, milk replacers include fat such as animal fat or vegetable oil, essential amino acids, vitamins and minerals.

In one aspect, a pre-weaned calf is a calf that is 56 days old or younger. In the case of goats and sheep, weaning is usually based on weight, however, weaning generally occurs at 6-8 weeks of age, or longer. Weaning of water buffalo is longer than cows, generally at 90 days or more.

Symptoms of respiratory disease include elevated rectal temperature, cough, nasal discharge, ocular discharge, and/or ear droop. Diarrhea can be caused by fecal pathogens including *Cryptosporidium parvum* and is frequently associated with a reduced appetite, abnormal attitude, dehydration, reduced weight gain, and/or decreased fecal pH. Respiratory disease and diarrhea are the two most important diseases of preweaned calves.

Fecal pH, specifically a neutral fecal pH, may be an indication of improved digestion and gastrointestinal health. In certain aspects, fecal pH can be used as an indication of the health of the gastrointestinal tract of a calf. A pH of 5.5 to 7.4 is indicative of a healthy calf, while a pH of less than 5.5 or greater than 7.4 may be indicative of digestive tract dysfunction.

In an embodiment, the subject is a herbivorous mammal, such as a bovine, an equine, an ovine, a caprine, a goat, a llama, an alpaca, a deer, an elk, or a pig.

In another embodiment, the subject is a companion animal, such as a dog, cat, rabbit, guinea pig, mini pig, hamster, or pet bird.

In yet another embodiment, the subject is a human.

In another embodiment, the subject is a fish, specifically a fish grown in aquaculture. As used herein, aquaculture means the active cultivation of aquatic organisms under controlled conditions. Aquaculture systems use water as the medium for cultivation. An aquaculture system must provide clean and oxygenated water to support the cultivated organisms as well as a means to remove deoxygenated water and wastes. As used herein, aquaculture includes both marine and freshwater aquaculture. Typical aquaculture systems include holding tanks and means for filtering, dissolved gas control, and temperature control. Aquaculture typically requires a prepared aquaculture feed composition to meet dietary requirements of the cultured animals.

Basal aquaculture fish feed compositions, for example, contain a protein source such as fish meal. Due to problems securing fish to produce fish meal and the depletion of fish stock for feeding fish, attempts have been made to supplement fish foods with other proteins. Soy protein is commonly used as a protein source in basal fish feeds, however soy protein induces gut inflammation and increases proinflammatory cytokines. Feeding fish the peptides and antibodies described herein can reduce gut inflammation in fish. Bacteria such as *Flavobacterium columnare* (catfish), *Yersinia ruckeri* (rainbow trout), *Flavobacterium psychrophilum* (trout and salmon), *Aeromonas hydrophila* (tilapia) have been shown to increase production of IL-10 during infection.

High valued fish for aquaculture applications (carp, tilapia, hybrid striped bass, salmon, trout, catfish, yellow perch, walleye; marine species such as cod, cobia, sea bass, tuna, and sole; and shellfish such as shrimp, scallops and oysters for example) may have poor larval growth and high rates of mortality, which is delaying the expansion of the aquaculture industry. In particular, there can be high mortality rates of up to 95% at the larval stage. Inflammation of the gastrointestinal tract has been shown to slow growth in fish species. New methods to improve fish growth are needed. The peptides and antibodies described herein can be added to a fish feed or a fish feed pre- or post-pellet formation and can either be added on the diet or as a replacement for some of the lipid in the fish food.

In an aspect, a method of reducing a foodborne or environmental pathogen in the intestines of a subject in need thereof comprises administering to the subject a composition comprising egg yolk, wherein the egg yolk the egg yolk comprises an antibody that specifically binds an IL-10 R2 peptide, wherein the isolated antibody is administered in an amount effective to reduce the foodborne or environmental pathogen in the intestines of the subject.

The compositions and methods described herein have the potential to eliminate the need for vaccinations for protozoa. By altering a key step in the immune response to protozoa, for example, the anti-IL-10 R2 antibodies improve the immune response to the infection without adverse effects. Current methods to control protozoan infection are drugs and attenuated vaccines. Attenuated vaccines have negative impacts on animal growth, while antibiotics are being phased out of animal feeds. Using an antibody to both IL-10 and its receptor may be more effective than either alone.

The invention is further illustrated by the following non-limiting examples.

EXAMPLES

Example 1: Design of IL-10 R1 and R2 Peptides

The sequences for chicken IL-10, IL-10 R1 and IL-10 R2 were sourced from pubmed.gov protein: CAF18432, CAJ15791.1, NP_990188.1. 8 amino acid peptide sequences were evaluated for their antigenicity using Bepipred 2.0 software and crystallography was utilized to determine antibody accessibility. Peptides were conjugated to bovine gamma globulin (BGG, Sigma, St. Louis, Mo.) using a glutaraldehyde procedure. The control vaccine and booster consisted of glutaraldehyde treated BGG and Freund's complete and incomplete adjuvants (Difco Laboratories, Detroit, Mich.), the same adjuvants used for making aIL-10 antibody. Hens were injected as previously described and eggs containing the antibody were collected beginning 21 days after the first injection, yolks separated, and dried by lyophilization. The presence of the antibody was determined using ELISA, where the coating peptide was attached to ovalbumin.

The IL-10 R1 peptides tested are given in Table 3:

TABLE 3

IL-10 R1 peptides

| Name | Peptide Sequence for Chicken | SEQ ID NO: |
|---|---|---|
| IL-10 Receptor 1: 1 | PGRDAPSD | 32 |
| IL-10 Receptor 1: 2 | GTNSPWTA | 33 |
| IL-10 Receptor 1: 3 | TNAFSPQE | 34 |
| IL-10 Receptor 1: 4 | RTVKYDDI | 35 |
| IL-10 Receptor 1: 5* | ISSSGSTD | 36 |
| IL-10 Receptor 1: 6* | HHRHSPAT | 37 |

The IL-10 R2 peptides are given in Table 4:

TABLE 4

IL-10 R2 peptides

| Name | Peptide Sequence for Chicken | SEQ ID NO: |
|---|---|---|
| IL-10 Receptor 2: 1 | VPKPRNAR | 14 |
| IL-10 Receptor 2: 2 | PPGVRKGN | 28 |
| IL-10 Receptor 2: 3 | ADTVIGPP | 38 |

Chick Experimentation: Five chick experiments were conducted to determine the neutralization efficacy of oral IgY antibodies to IL-10 R1 and IL-10 R2. Day-old broiler pullets from Welp Hatchery, Bancroft, Iowa, were divided into five chicks/pen and housed in a battery brooder with raised wire floors. Ten pens of chicks were assigned to each treatment in an antibody X coccidia infection factorial arrangement in a complete randomized design. Diets consisted of a standard broiler starter diet supplemented with either control dried egg yolk antibody (from hens injected with BGG carrier in adjuvant) or an aIL-10/aIL-10 R1/aIL-10 R2 peptide dried egg yolk antibody (3.41 g/Kg diet). Since peptide antibody replaced control antibody containing the exact same nutrient profiles (nutrient profiles of dried egg yolk powder), the nutrient content of all diets were identical and came from the same lot of feed. The dietary level of anti-IL-10 antibody was a level that prevented *Eimeria*-induced growth depression in chicks. Chicks assigned each diet treatment were either orally gavaged with a saline solution or an Advent Coccidiosis vaccine (10× vaccine dose consisting of a proprietary blend of live attenuated *Eimeria acervulina*, *Eimeria maxima*, and *Eimeria tenella* oocysts, Huvepharma, Sofia, Bulgaria) at 3 d. Chicks and feed were weighed on days 7, 14 and 21. Feed conversion was calculated by dividing feed consumption by body weight over the 21-day period. Fecal samples were collected from each pen on day 7 post infection. Oocysts per gram of feces were quantified using the McMaster technique.

Table 5 provides the oral antibodies used in each experiment.

TABLE 5

Oral antibodies evaluated in each xxperiment

| Experiment Number | Antibodies Evaluated |
|---|---|
| Experiment 1 | Control, aIL-10 R1:2, aIL-10 R1:4, aIL-10 R1:5 |
| Experiment 2 | Control, aIL-10 R1:1, aIL-10 R1:3, aIL-10 R1:6 |
| Experiment 3 | Control, aIL-10 R1:5, aIL-10 R1:6 |
| Experiment 4 | Control, aIL-10 R2:1, aIL-10 R2:2, aIL-10 R2:3 |
| Experiment 5 | Control, aIL-10, aIL-10 R2:1, aIL-10 R2:2 |

Statistical Analysis: The experiments were set up in a completely randomized factorial design and analyzed as a two-way ANOVA using ANOVAs PROC MIXED of SAS 9.4 (SAS Institute Inc., Cary, N.C.). The LSD test was used for multiple treatment comparisons using the LSMEANS statement of SAS 9.4 with letter grouping obtained using the SAS pdmix800 macro. For the different statistical tests, significance was declared at a P-value of $\leq 0.05$. Post hoc analyses for treatment differences were conducted if interactions were significant.

Immunohistochemistry Staining: Previously collected paraffin sections with known mucosal IL-10 elevation compared to uninfected birds were used to demonstrate IL-10 R1 and IL-10 R2 presence. Slides were of the duodenum of 26 day old birds either infected with coccidia or a control saline gavage on day 21 as described above. Slides were incubated overnight at 60° C. before being deparaffinized with two changes of xylene for 10 minutes, and rehydrated with isopropyl alcohol at two changes of 100% alcohol, two changes of 95% alcohol, one change of 75% alcohol, and one change of distilled water at 1 min per change. Slides underwent heat induced epitope-retrieval (HIER) in tris urea solution. After rinsing with tris buffered saline solution, an ImmEdge™ pen (Vector Laboratories, Inc., Burlingame, Calif.) was used to isolate tissue sections and were submerged with blocking buffer for 1 hour in a humidified chamber.

To articulate IL-10 R1, tissues were coated in rabbit anti-IL-10 R1 polyclonal antibody (GeneTex, Irvine, Calif.) at 1:300 dilution in blocking buffer overnight at 4° C. in a humidified dark enclosure. Slides were then stained with 1:100 diluted Donkey anti-rabbit Dylight®594 (Bethyl, Montgomery, Tex.) for one hour in a humidified chamber. Nuclei were highlighted by Fluoro-Gel with tris buffer and 4',6-diamidino-2-phenylindole (DAPI) solution.

To articulate IL-10 R2, a contiguous intestinal section was coated in rabbit anti-IL-10 R2 polyclonal antibody (GeneTex, Irvine, Calif.) at 1:100 dilution in blocking buffer overnight at 4° C. in a humidified dark enclosure. Slides were then stained with 1:100 diluted Donkey anti-rabbit Dylight®594 (Bethyl, Montgomery, Tex.) for one hour in a humidified chamber. Nuclei were highlighted by Fluoro-Gel with tris buffer and DAPI solution. Due to *Eimeria* oocyst wall autofluorescence at 495 nm, only the red channel was used for immunofluorescence and the blue channel was used for cell nuclei. Slides were imaged using a Nikon Eclipse E600 with Y-FL fluorescence attachment microscope.

Example 1: Broiler Performance with Oral IL-10 R1 Antibody Administration

Each of the six IL-10 R1 antibodies tested had no significant effect on chick weight compared to chicks fed the control antibody. Throughout the 21 days of treatment with IL-10 R1 antibodies 1-6, the chicks in studies 1 and 2 had no significant body weight differences after coccidia infection compared to the control (Table 6 and 7). A lower dose of *Eimeria* was used in study 3, and while no coccidiosis effect was observed at day 21, there was a significant weight loss on days 10 and 14 (p<0.05), indicating coccidia infection (Table 8). However, neither of the IL-10 R1 antibodies re-tested in study had any anti-coccidia effect.

TABLE 6

Study 1 of anti-IL-10 R1 antibodies in chickens

| Study 1 | Individual Chick Weight (g) | | | Feed Conversion | | | Oocyst count |
|---|---|---|---|---|---|---|---|
| | Uninfected | Coccidia Infected | Antibody Main Effect | Uninfected | Coccidia Infected | Antibody Main Effect | Oocysts/ gram feces* |
| Control | 790 | 663 | $726^A$ | 1.452 | 1.572 | $1.512^B$ | $316236^B$ |
| aIL-10 R1:2 | 762 | 636 | $699^A$ | 1.531 | 1.723 | $1.627^A$ | $307109^B$ |
| aIL-10 R1:4 | 780 | 657 | $718^A$ | 1.522 | 1.73 | $1.626^{AB}$ | $388711^A$ |
| aIL-10 R1:5 | 677 | 593 | $635^B$ | 1.644 | 1.746 | $1.695^A$ | $535654^B$ |
| SEM | 21 | | 0.055 | | | | |

TABLE 6-continued

Study 1 of anti-IL-10 R1 antibodies in chickens

| Study 1 | Individual Chick Weight (g) | | | Feed Conversion | | | Oocyst count |
|---|---|---|---|---|---|---|---|
| | Uninfected | Coccidia Infected | Antibody Main Effect | Uninfected | Coccidia Infected | Antibody Main Effect | Oocysts/ gram feces* |
| | P Values | | | | | | |
| Antibody | <0.0001 | | | 0.02 | | | 0.003 |
| Coccidiosis | <0.0001 | | | 0.0003 | | | <0.0001 |
| Antibody × Coccidiosis | 0.7 | | | 0.74 | | | 0.003 |

A-B Means with different superscripts within a column were significantly different (P < 0.05).
Average weight (n = 10) and feed consumption (n = 10) were measured in grams.
SEM = Standard error of the mean.
Feed conversion is calculated by dividing feed consumption by average pen body weight.
*All uninfected pens had oocyst counts of 0 oocysts per gram of feces.
Only coccidia infected groups are shown in the table.

TABLE 7

Study 2 IL-10 Receptor 1 antibodies 1, 3 and 6

| Study 2 | Individual Chick Weight (g) | | Feed Conversion | | Oocyst count Oocyst/ gram feces* |
|---|---|---|---|---|---|
| | Uninfected | Coccidia Infected | Uninfected | Coccidia Infected | |
| Control | 735 | 639 | 1.678 | 1.877 | 657688 |
| aIL-10 R1:1 | 710 | 655 | 1.682 | 1.74 | 327232 |
| aIL-10 R1:3 | 711 | 676 | 1.674 | 1.751 | 360146 |
| aIL-10 R1:6 | 731 | 656 | 1.685 | 1.593 | 522890 |
| SEM | 21 | | 0.071 | | 93221 |
| | P Values | | | | |
| Antibody | 0.94 | | 0.17 | | 0.26 |
| Coccidiosis | <0.0001 | | 0.15 | | <0.0001 |
| Antibody × Coccidiosis | 0.53 | | 0.13 | | 0.26 |

Average weight (n = 10) and feed consumption (n = 10) were measured in grams. SEM = Standard error of the mean. Feed conversion is calculated by dividing feed consumption by average pen body weight.
*All uninfected pens had oocyst counts of 0 oocysts per gram of feces. Only coccidia infected groups are shown in the table.

TABLE 8

Study 3 IL-10 Receptor 1 Antibodies 5 and 6

| Study 3 | Day 10 Chick Weight | Day 14 Chick Weight | Day 21 | | | |
|---|---|---|---|---|---|---|
| | | | Chick Weight | Feed Conversion | FC Antibody Main Effect | Oocyst/g feces* |
| Control Uninfected | 199 | 386 | 698 | 1.411 | 1.421[B] | 0 |
| Control Infected | 178 | 341 | 634 | 1.43 | | 309184 |
| R1:5 Uninfected | 206 | 372 | 645 | 1.473 | 1.471[A] | 0 |
| R1:5 Infected | 181 | 341 | 657 | 1.469 | | 317882 |
| R1:6 Uninfected | 192 | 361 | 631 | 1.469 | 1.450[AB] | 0 |
| R1:6 Infected | 170 | 338 | 650 | 1.431 | | 449404 |
| Standard Error of the Mean | 6 | 12 | 27 | 0.017 | | |
| | P values | | | | | |
| Antibody | 0.15 | 0.49 | 0.51 | 0.02 | | 0.0866 |
| Coccidiosis | <0.0001 | 0.0009 | 0.57 | 0.58 | | <0.0001 |
| Antibody × Coccidiosis | 0.94 | 0.65 | 0.13 | 0.23 | | 0.0866 |

[A-B]Means with different superscripts within a column were significantly different (P < 0.05).
Average weight (n =10) and feed consumption (n = 10) were measured in grams.
SEM = Standard error of the mean.
Feed conversion is calculated by dividing feed consumption by average pen body weight.

None of the six IL-10 R1 antibodies tested recovered the losses associated with coccidiosis infection or reduced oocyst shedding. In study 1, aIL-10 R1:2 and 5 diets had a negative impact on feed conversion. aIL-10 R1:5 had increased oocyst shedding and a negative impact on growth rate with a 12% reduction in average chick weight compared to control fed chicks (p<0.0001, Table 6). Study 2 showed no effects of aIL-10 R1:1, 3 and 6. Due to the trend of aIL-10 R1:6 fed, coccidia infected birds to have a 15% improved feed conversion compared to control antibody fed, coccidia infected birds; aIL-10R1:6 treatment was repeated in study 3. In study 3, aIL-10 R1:5 administration during coccidia infection was repeated and although there was not a similar decrease in chick weight due to the aIL-10 R1:5 antibody, it still had a negative impact on feed conversion compared to control (Table 8). IL-10 R1 oral antibody administration did not ameliorate negative coccidia symptoms, and in the case of aIL-10 R1:2 and 5 had a negative impact on the growth rate and feed conversion of the bird.

Example 2: Broiler Performance with Oral IL-10 R2 Antibody Administration

In studies 4 and 5, birds infected with *Eimeria* gained significantly less weight and had an increased feed conversion ratio compared to uninfected birds (Table 9 and 10). In study 4, infected chicks fed aIL-10 R2:1 or aIL-10 R2:2 overcame the coccidia infection and had similar 21-day body weight to uninfected chicks (trend, p=0.07). No main effect due to the dietary antibody was present in either study. Oral antibody administration had no effect on oocyst shedding in *Eimeria* infected treatment groups. In study 5, uninfected, aIL-10 fed chicks gained significantly less weight compared to uninfected, control antibody fed chicks (Table 10). In study 5, infected control fed birds had a 131-gram difference in weight gain compared to uninfected control fed birds. In comparison to control fed birds, aIL-10 had significantly less difference in weight gain between coccidia treatments, indicating aIL-10 had a positive effect on growth rate during coccidia infection. Overall, none of the antibodies to IL-10 R1 affected the weight gain of *Eimeria* infected birds, while aIL-10 R2:1 and aIL-10 R2:2 showed promising results similar to aIL-10.

TABLE 9

Study 4 IL-10 Receptor 2 Antibodies 1, 2 and 3

| Study 4 | Individual Chick Weight (g) | | Feed Conversion (by pen) | | Oocyst count |
|---|---|---|---|---|---|
| | Uninfected | Coccidia Infected | Oocyst/gram feces | Coccidia Infected | Oocyst/g feces* |
| FCA | 684$^a$ | 585$^c$ | 1.468 | 1.533 | 622918 |
| aIL-10 R2:1 | 679$^a$ | 663$^a$ | 1.511 | 1.516 | 614536 |
| aIL-10 R2:2 | 659$^a$ | 646$^{ab}$ | 1.405 | 1.495 | 486347 |
| aIL-10 R2:3 | 668$^a$ | 604$^{ab}$ | 1.459 | 1.53 | 866860 |
| SEM | 19 | | 0.034 | | 132053 |
| P Values | | | | | |
| Antibody | 0.17 | | 0.27 | | 0.73 |
| Coccidiosis | 0.0003 | | 0.04 | | <0.0001 |
| Antibody x Coccidiosis | 0.0692 | | 0.62 | | 0.73 |

$^{a-c}$Means with different superscripts within a column had a trend (P < 0.10). Average weight (n = 10) and feed consumption (n = 10) were measured in grams. SEM = Standard error of the mean. Feed conversion is calculated by dividing feed consumption by average pen body weight.
*All uninfected pens had oocyst counts of 0 oocysts per gram of feces.
Only coccidia infected groups are shown in the table.

TABLE 10

Study 5 IL-10 Receptor 2 Antibodies 1 and 2

| Study 5 | Individual Chick Weight (g) | | Feed Conversion | | Oocyst Count Oocyst |
|---|---|---|---|---|---|
| | Uninfected | Coccidia Infected | Uninfected | Coccidia Infected | Count/g feces* |
| Control | 709$^A$ | 578$^C$ | 1.523 | 1.569 | 195031 |
| aIL-10 | 662$^B$ | 595$^C$ | 1.484 | 1.498 | 374626 |
| aIL-10 R2:1 | 681$^{AB}$ | 598$^C$ | 1.508 | 1.564 | 245589 |
| aIL-10 R2:2 | 701$^A$ | 606$^C$ | 1.446 | 1.548 | 166483 |
| SEM | 11 | | 0.028 | | 35037 |
| P Values | | | | | |
| Antibody | 0.24 | | 0.14 | | 0.46 |
| Coccidiosis | <0.0001 | | <0.0001 | | <0.0001 |
| Antibody x Coccidiosis | 0.0478 | | 0.71 | | 0.46 |

$^{A-C}$Means with different superscripts within a column were significantly different (P < 0.05). Average weight (n = 10) and feed consumption (n = 10) were measured in grams.
SEM = Standard error of the mean.
Feed conversion is calculated by dividing feed consumption by average pen body weight.
*All uninfected pens had oocyst counts of 0 oocysts per gram of feces.
Only coccidia infected groups are shown in the table.

Example 3: Intestinal Mucosal IL-10 Receptor 1 and 2 Presence

To further elucidate why aIL-10 R2 is more beneficial than aIL-10 R1, immunohistochemistry was done to evaluate IL-10 R1 and IL-10 R2 presence during *Eimeria* infection. While both 10-10 R1 and R2 are of low abundance in uninfected chicks, on day 5 post infection in the duodenum, IL-10 R1 is visually lower in presence compared to the IL-10 R2 shown in red (data not shown). The increased presence of IL-10 R2 staining illustrates that it is more prominent in the intestinal mucosa and surrounding coccidia infected regions when compared to IL-10 R1. IL-10 R2 presence was objectively higher in birds infected with *Eimeria* compared to control birds. This result indicates that IL-10R2 may be playing an additional role during *Eimeria* infection in chickens.

Discussion

Feeding *Eimeria* infected chicks aIL-10 has previously been shown to prevent reduced body weight compared to challenged chicks fed control antibody. In this experiment, we did not observe the prevention of reduced growth rate when chicks were fed an antibody to IL-10 Receptor 1. However, we did observe improvement with administration of an oral antibody to IL-10 Receptor 2, indicating IL-10 receptor complex IL-10 R2 binding is critical for the anti-inflammatory signaling pathway potentially upregulated by coccidia. The binding site of aIL-10 (VLPRAMQT; SEQ ID NO: 39) is not located near the IL-10 Receptor binding region so direct allosteric hindrance of the aIL-10 antibody to IL-10 R1 does not explain the ability of aIL-10 to neutralize IL-10. As shown previously in the art, a monoclonal antibody to a noncontiguous peptide sequence on IL-10, which overlaps with the VLPRAMQT region, also showed that antibody binding to this specific IL-10 region resulted in a noncompetitive binding to the IL-10 R1 receptor. Even through this noncompetitive binding, the monoclonal antibody was able to neutralize IL-10 function. The monoclonal binding was capable of interfering with conformational changes in the IL-10/IL-10 R1 complex. Without being held to theory, we hypothesize that the aIL-10 binding peptide region does not interfere with IL-10R1 binding, but may inhibit the ability of the IL-10/IL-10 R1 complex binding IL-10 R2.

The IL-10 R2 presence was greater than IL-10 R1 in the *Eimeria* infected duodenum (data not shown). The prominence of IL-10 R2 expression during coccidia infection may indicate it has an additional role during coccidia invasion and replication. While IL-10R1 is faithful to IL-10, IL-10R2 is promiscuous and interacts in other cytokine signaling pathways, including IL-22, IL-26, IL-28A, IL-28B and IL-29. Feeding an oral antibody to IL-10 R2 may have an effect on these related cytokine pathways as well. IL-22 has been shown to drive intestinal immunopathology associated with many related apicomplexan parasites, including the closely related *Eimeria falciformis*. Chicken IL-26 was cloned in 2016, and was found to induce proinflammatory cytokines. The role of IL-26 during *Eimeria* infection has not been well studied, but it has been associated with exacerbation of pathology in a parasitic disease in humans, lymphatic filariasis. IL-28A, IL-28B and IL-29 are all part of the interferon λ (IFNλ) signaling cascade. The role of IFNλ during *Eimeria* infection has not been elucidated, but IFNλ is critical for the control of related parasites. IL-10R2 neutralization by aIL-10R2:1 and aIL-10R2:2 may have an effect on these pro-inflammatory cytokine pathways and reduce *Eimeria* associated inflammation and immunopathology resulting in the therapeutic effects of aIL-10R2:1 and aIL-10R2:2.

aIL-10 R1:5 was observed to have a negative effect on growth rate and feed conversion, and resulted in a larger number of oocysts shed per gram of feces (Tables 6 and 8). The negative effect on intestinal absorptive function is likely due to the importance of IL-10 signaling to maintain normal intestinal mucosal immune homeostasis and increased parasite burden reflected by the increased number of oocysts shed per gram of feces. IL-10 knockout mice are used as a model organism to study Crohn's disease and exhibit colitis associated with the absence of functional IL-10 within the intestine. Neutralization of IL-10 receptor 1 by feeding aIL-10 R1:5 exerts similar effects on intestines exhibited by lack of weight gain in this study. A potential reason for the effects of aIL-10 R1:5 on weight gain and feed conversion in both infected and uninfected birds could potentially be an overdose of the antibody, resulting in the inability to properly mediate the intestinal host microbiota relationship.

aIL-10 R2:1 and aIL-10R2:2 were shown to potentially ameliorate negative coccidiosis symptoms. In study 4, these antibodies demonstrated positive effects on weight gain equivalent to previous aIL-10 studies. To evaluate the effect of aIL-10R2:1 and aIL-10R2:2 in direct comparison to aIL-10, study 5 was performed. In study 5, the coccidia vaccine was less than one-month old resulting in a greater virulence and had more detrimental effects on chick weight at day 21 of age than in previous studies 1-4. In addition, high titer aIL-10 was fed at a dose ten times that currently commercially used to be equivalent in dose to aIL-10R2 antibodies. The high dose of aIL-10 likely resulted in an overdose of antibody evident in the 70 gram mean chick weight difference between uninfected control and uninfected aIL-10 fed chicks. Nevertheless, aIL-10 fed birds had a significantly decreased difference in weight loss due to coccidia infection compared to control (FIG. 1), indicating aIL-10 was protective against coccidia related lack of weight gain despite its confounding negative effects on uninfected bird weight.

In conclusion, IL-10 R2:1 is a promising alternative anti-coccidial immunotherapeutic. Study 5 results indicate that aIL-10 is better than either of the IL-10 R2 antibodies at reducing the effect of coccidia infection on weight gain. In future studies the dose of aIL-10 R2:1 will be honed and birds will be fed aIL-10 and aIL-10 R2:1 in combination to evaluate if the combination therapy improves efficacy and decreases dose.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. An interleukin-10 receptor-2 peptide covalently linked to a carrier peptide, wherein the interleukin-10 receptor-2 peptide consists of an 8-15 amino acid sequence that includes SEQ ID NO: 1 ((I/V)P(P/K/V/E)P(E/K/R/Q)N(A/V)R), SEQ ID NO: 2 ((S/L/V)PAF(A/P)(K/Q)(G/T/E)(N/T/D)), or SEQ ID NO: 3 (PP(G/T/Q/V)(V/T/A)(R/H/T/S)(GN/NHP/SAA)).

2. An interleukin-10 receptor-2 peptide covalently linked to a carrier peptide, wherein the interleukin-10 receptor-2 peptide consists of an 8-15 amino acid sequence that includes one of SEQ ID NOs: 4, 5, 8, 9, 12-21, and 24-31.

* * * * *

SEQUENCE LISTING

<160> NUMBER OF SEQ ID NOS: 39

<210> SEQ ID NO 1
<211> LENGTH: 8
<212> TYPE: PRT
<213> ORGANISM: Artificial Sequence
<220> FEATURE:
<223> OTHER INFORMATION: IL-10 R2 peptide
<220> FEATURE:
<221> NAME/KEY: variant
<222> LOCATION: (1)..(1)
<223> OTHER INFORMATION: X1 is I or V
<220> FEATURE:
<221> NAME/KEY: variant
<222> LOCATION: (3)..(3)
<223> OTHER INFORMATION: X3 is P or K or V or E
<220> FEATURE:
<221> NAME/KEY: variant
<222> LOCATION: (5)..(5)
<223> OTHER INFORMATION: X5 is E or K or R or Q
<220> FEATURE:
<221> NAME/KEY: variant
<222> LOCATION: (7)..(7)
<223> OTHER INFORMATION: X7 is A or V

<400> SEQUENCE: 1

Xaa Pro Xaa Pro Xaa Asn Xaa Arg
1               5

<210> SEQ ID NO 2
<211> LENGTH: 8
<212> TYPE: PRT
<213> ORGANISM: Artificial Sequence
<220> FEATURE:
<223> OTHER INFORMATION: IL-10 R2 peptide
<220> FEATURE:
<221> NAME/KEY: variant
<222> LOCATION: (1)..(1)
<223> OTHER INFORMATION: X1 is S or L or V
<220> FEATURE:
<221> NAME/KEY: variant
<222> LOCATION: (5)..(5)
<223> OTHER INFORMATION: X5 is A or P
<220> FEATURE:
<221> NAME/KEY: variant
<222> LOCATION: (6)..(6)
<223> OTHER INFORMATION: X6 is K or Q
<220> FEATURE:
<221> NAME/KEY: variant
<222> LOCATION: (7)..(7)
<223> OTHER INFORMATION: X7 is G or T or E
<220> FEATURE:
<221> NAME/KEY: variant
<222> LOCATION: (8)..(8)
<223> OTHER INFORMATION: X8 is N or T or D

<400> SEQUENCE: 2

Xaa Pro Ala Phe Xaa Xaa Xaa Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: IL-10 R2 peptide
<220> FEATURE:
<221> NAME/KEY: variant
<222> LOCATION: (3)..(3)
<223> OTHER INFORMATION: X3 is G or T or Q or V
<220> FEATURE:
<221> NAME/KEY: variant
<222> LOCATION: (4)..(4)
<223> OTHER INFORMATION: X4 is V or T or A

```
<220> FEATURE:
<221> NAME/KEY: variant
<222> LOCATION: (5)..(5)
<223> OTHER INFORMATION: X5 is R or H ot T or S
<220> FEATURE:
<221> NAME/KEY: variant
<222> LOCATION: (5)..(5)
<223> OTHER INFORMATION: X5 is R or H or T or S
<220> FEATURE:
<221> NAME/KEY: variant
<222> LOCATION: (6)..(6)
<223> OTHER INFORMATION: X6 is G or N
<220> FEATURE:
<221> NAME/KEY: variant
<222> LOCATION: (7)..(7)
<223> OTHER INFORMATION: X7 is GN or NHP or SAA

<400> SEQUENCE: 3

Pro Pro Xaa Xaa Xaa Xaa Xaa
1               5

<210> SEQ ID NO 4
<211> LENGTH: 8
<212> TYPE: PRT
<213> ORGANISM: Homo sapiens

<400> SEQUENCE: 4

Val Pro Pro Pro Glu Asn Val Arg
1               5

<210> SEQ ID NO 5
<211> LENGTH: 8
<212> TYPE: PRT
<213> ORGANISM: Canis lupus

<400> SEQUENCE: 5

Val Pro Pro Pro Lys Asn Val Arg
1               5

<210> SEQ ID NO 6
<211> LENGTH: 8
<212> TYPE: PRT
<213> ORGANISM: Felis catus

<400> SEQUENCE: 6

Val Pro Pro Pro Glu Asn Val Arg
1               5

<210> SEQ ID NO 7
<211> LENGTH: 8
<212> TYPE: PRT
<213> ORGANISM: Bos taurus

<400> SEQUENCE: 7

Val Pro Pro Pro Glu Asn Val Arg
1               5

<210> SEQ ID NO 8
<211> LENGTH: 8
<212> TYPE: PRT
<213> ORGANISM: Ovis aries

<400> SEQUENCE: 8

Ile Pro Pro Pro Glu Asn Val Arg
1               5

<210> SEQ ID NO 9
```

```
<211> LENGTH: 8
<212> TYPE: PRT
<213> ORGANISM: Capra hircus

<400> SEQUENCE: 9

Ile Pro Pro Pro Glu Asn Val Arg
1               5

<210> SEQ ID NO 10
<211> LENGTH: 8
<212> TYPE: PRT
<213> ORGANISM: Equus caballus

<400> SEQUENCE: 10

Val Pro Pro Pro Glu Asn Val Arg
1               5

<210> SEQ ID NO 11
<211> LENGTH: 8
<212> TYPE: PRT
<213> ORGANISM: Sus scrofa

<400> SEQUENCE: 11

Val Pro Pro Pro Glu Asn Val Arg
1               5

<210> SEQ ID NO 12
<211> LENGTH: 8
<212> TYPE: PRT
<213> ORGANISM: Mus musculus

<400> SEQUENCE: 12

Ile Pro Pro Pro Glu Lys Val Arg
1               5

<210> SEQ ID NO 13
<211> LENGTH: 8
<212> TYPE: PRT
<213> ORGANISM: Rattus norvegicus

<400> SEQUENCE: 13

Ile Pro Pro Pro Glu Asn Val Arg
1               5

<210> SEQ ID NO 14
<211> LENGTH: 8
<212> TYPE: PRT
<213> ORGANISM: Gallus gallus

<400> SEQUENCE: 14

Val Pro Lys Pro Arg Asn Ala Arg
1               5

<210> SEQ ID NO 15
<211> LENGTH: 8
<212> TYPE: PRT
<213> ORGANISM: Meleagris gallopavo

<400> SEQUENCE: 15

Val Pro Lys Pro Arg Asn Ala Arg
1               5

<210> SEQ ID NO 16
<211> LENGTH: 8
<212> TYPE: PRT
```

-continued

<213> ORGANISM: Danio rerio

<400> SEQUENCE: 16

Val Pro Val Pro Glu Asn Val Arg
1               5

<210> SEQ ID NO 17
<211> LENGTH: 8
<212> TYPE: PRT
<213> ORGANISM: Xenopus tropicalis

<400> SEQUENCE: 17

Val Pro Glu Pro Gln Asn Val Arg
1               5

<210> SEQ ID NO 18
<211> LENGTH: 8
<212> TYPE: PRT
<213> ORGANISM: Homo sapiens

<400> SEQUENCE: 18

Ser Pro Ala Phe Ala Lys Gly Asn
1               5

<210> SEQ ID NO 19
<211> LENGTH: 8
<212> TYPE: PRT
<213> ORGANISM: Canis lupus

<400> SEQUENCE: 19

Leu Pro Ala Phe Pro Lys Gly Thr
1               5

<210> SEQ ID NO 20
<211> LENGTH: 8
<212> TYPE: PRT
<213> ORGANISM: Felis catus

<400> SEQUENCE: 20

Val Pro Ala Phe Pro Lys Gly Asn
1               5

<210> SEQ ID NO 21
<211> LENGTH: 8
<212> TYPE: PRT
<213> ORGANISM: Bos taurus

<400> SEQUENCE: 21

Ser Pro Ala Phe Pro Lys Gly Asn
1               5

<210> SEQ ID NO 22
<211> LENGTH: 8
<212> TYPE: PRT
<213> ORGANISM: Ovis aries

<400> SEQUENCE: 22

Ser Pro Ala Phe Pro Lys Gly Asn
1               5

<210> SEQ ID NO 23
<211> LENGTH: 8
<212> TYPE: PRT
<213> ORGANISM: Capra hircus

```
<400> SEQUENCE: 23

Ser Pro Ala Phe Pro Lys Gly Asn
1               5

<210> SEQ ID NO 24
<211> LENGTH: 8
<212> TYPE: PRT
<213> ORGANISM: Equus caballus

<400> SEQUENCE: 24

Ser Pro Ala Phe Pro Lys Gly Asp
1               5

<210> SEQ ID NO 25
<211> LENGTH: 8
<212> TYPE: PRT
<213> ORGANISM: Sus scrofa

<400> SEQUENCE: 25

Ser Pro Ala Phe Pro Gln Gly Asp
1               5

<210> SEQ ID NO 26
<211> LENGTH: 8
<212> TYPE: PRT
<213> ORGANISM: Mus musculus

<400> SEQUENCE: 26

Val Pro Ala Phe Pro Lys Thr Asn
1               5

<210> SEQ ID NO 27
<211> LENGTH: 8
<212> TYPE: PRT
<213> ORGANISM: Rattus norvegicus

<400> SEQUENCE: 27

Val Pro Ala Phe Pro Lys Glu Asn
1               5

<210> SEQ ID NO 28
<211> LENGTH: 8
<212> TYPE: PRT
<213> ORGANISM: Gallus gallus

<400> SEQUENCE: 28

Pro Pro Gly Val Arg Lys Gly Asn
1               5

<210> SEQ ID NO 29
<211> LENGTH: 8
<212> TYPE: PRT
<213> ORGANISM: Meleagris gallopavo

<400> SEQUENCE: 29

Pro Pro Thr Val His Lys Gly Asn
1               5

<210> SEQ ID NO 30
<211> LENGTH: 9
<212> TYPE: PRT
<213> ORGANISM: Danio rerio

<400> SEQUENCE: 30
```

Pro Pro Gln Thr Thr Asn Asn His Pro
1               5

<210> SEQ ID NO 31
<211> LENGTH: 9
<212> TYPE: PRT
<213> ORGANISM: Xenopus tropicalis

<400> SEQUENCE: 31

Pro Pro Val Ala Ser Gly Ser Ala Ala
1               5

<210> SEQ ID NO 32
<211> LENGTH: 8
<212> TYPE: PRT
<213> ORGANISM: Gallus gallus

<400> SEQUENCE: 32

Pro Gly Arg Asp Ala Pro Ser Asp
1               5

<210> SEQ ID NO 33
<211> LENGTH: 8
<212> TYPE: PRT
<213> ORGANISM: Gallus gallus

<400> SEQUENCE: 33

Gly Thr Asn Ser Pro Trp Thr Ala
1               5

<210> SEQ ID NO 34
<211> LENGTH: 8
<212> TYPE: PRT
<213> ORGANISM: Gallus gallus

<400> SEQUENCE: 34

Thr Asn Ala Phe Ser Pro Gln Glu
1               5

<210> SEQ ID NO 35
<211> LENGTH: 8
<212> TYPE: PRT
<213> ORGANISM: Gallus gallus

<400> SEQUENCE: 35

Arg Thr Val Lys Tyr Asp Asp Ile
1               5

<210> SEQ ID NO 36
<211> LENGTH: 8
<212> TYPE: PRT
<213> ORGANISM: Gallus gallus

<400> SEQUENCE: 36

Ile Ser Ser Ser Gly Ser Thr Asp
1               5

<210> SEQ ID NO 37
<211> LENGTH: 8
<212> TYPE: PRT
<213> ORGANISM: Gallus gallus

<400> SEQUENCE: 37

His His Arg His Ser Pro Ala Thr
1               5

```
<210> SEQ ID NO 38
<211> LENGTH: 8
<212> TYPE: PRT
<213> ORGANISM: Gallus gallus

<400> SEQUENCE: 38

Ala Asp Thr Val Ile Gly Pro Pro
1               5

<210> SEQ ID NO 39
<211> LENGTH: 8
<212> TYPE: PRT
<213> ORGANISM: Gallus gallus

<400> SEQUENCE: 39

Val Leu Pro Arg Ala Met Gln Thr
1               5
```